United States Patent
Kotidis et al.

(10) Patent No.: US 9,983,126 B2
(45) Date of Patent: May 29, 2018

(54) QUANTUM CASCADE LASER (QCL) BASED GAS SENSING SYSTEM AND METHOD

(71) Applicant: Block Engineering, LLC, Marlborough, MA (US)

(72) Inventors: Petros Kotidis, Framingham, MA (US); Erik Deutsch, Brookline, MA (US); Hongke Ye, Chelmsford, MA (US); Alexander Mazurenko, Dover, MA (US); Anish K. Goyal, Marlborough, MA (US); Jeffrey S. Socha, Boylston, MA (US)

(73) Assignee: Block Engineering, LLC, Marlborough, MA (US)

( * ) Notice: Subject to any disclaimer, the term of this patent is extended or adjusted under 35 U.S.C. 154(b) by 0 days. days.

(21) Appl. No.: 15/017,610

(22) Filed: Feb. 6, 2016

(65) Prior Publication Data

US 2016/0231239 A1    Aug. 11, 2016

Related U.S. Application Data

(60) Provisional application No. 62/262,010, filed on Dec. 2, 2015, provisional application No. 62/186,067, filed
(Continued)

(51) Int. Cl.
*G01N 21/00* (2006.01)
*G01N 21/39* (2006.01)
(Continued)

(52) U.S. Cl.
CPC ............. *G01N 21/39* (2013.01); *G01J 3/108* (2013.01); *G01J 3/433* (2013.01); *H01S 5/0622* (2013.01);
(Continued)

(58) Field of Classification Search
CPC . G01B 11/2504; G01B 11/24; G01B 11/2518; G01B 21/042; G01B 11/002;
(Continued)

(56) References Cited

U.S. PATENT DOCUMENTS 5,317,156 A  *  5/1994  Cooper .................. G01N 21/39
                                                   250/339.13
5,877,862 A     3/1999  Nelson et al.
(Continued)

FOREIGN PATENT DOCUMENTS

DE    10 2007 062 651 A1    6/2009
WO       2010062752 A1    6/2010

OTHER PUBLICATIONS

International Search Report and Written Opinion of the International Searching Authority, dated Jun. 9, 2016, from International Application No. PCT/US2016/016909, filed on Feb. 6, 2016. Thirteen pages.
(Continued)

*Primary Examiner* — Michael P Stafira
(74) *Attorney, Agent, or Firm* — HoustonHogle LLP

(57) ABSTRACT

A system and method are disclosed for gas sensing over a wide tunable wavelength range provided by one or more quantum cascade lasers. A laser beam is generated within the wide tunable wavelength range, which is given by the sum of the wavelength ranges from the individual lasers. Gas sensing or detection is achieved by obtaining an infrared absorption spectrum for a sample contained in one or more cells having different path lengths for the laser beam.

19 Claims, 17 Drawing Sheets

Related U.S. Application Data on Jun. 29, 2015, provisional application No. 62/113,069, filed on Feb. 6, 2015.

(51) Int. Cl.

| | |
|---|---|
| *H01S 5/34* | (2006.01) |
| *H01S 5/062* | (2006.01) |
| *G01J 3/433* | (2006.01) |
| *G01J 3/10* | (2006.01) |
| G01N 21/3504 | (2014.01) |
| H01S 5/40 | (2006.01) |
| G01N 21/03 | (2006.01) |
| G01N 21/17 | (2006.01) |

(52) U.S. Cl.
CPC .......... *H01S 5/3401* (2013.01); *G01N 21/031* (2013.01); *G01N 21/3504* (2013.01); *G01N 2021/1704* (2013.01); *G01N 2021/3513* (2013.01); *G01N 2021/399* (2013.01); *G01N 2201/0612* (2013.01); *H01S 5/4012* (2013.01); *H01S 5/4025* (2013.01); *H01S 5/4087* (2013.01)

(58) Field of Classification Search
CPC ... G01B 11/245; G01B 11/03; G01B 11/2513; G01B 9/02072; G01B 9/0209; G01B 11/00; G01B 11/14; G01B 11/2441; G01B 11/25
See application file for complete search history.

(56) References Cited

U.S. PATENT DOCUMENTS

| | | | |
|---|---|---|---|
| 6,627,412 B1 | 9/2003 | Manning et al. | |
| 6,737,651 B1 | 5/2004 | Lendl | |
| 7,115,869 B2 | 10/2006 | Shelley et al. | |
| 7,697,976 B2 | 4/2010 | Wu et al. | |
| 8,264,690 B2* | 9/2012 | Rao | G01N 21/39 356/437 |
| 9,329,085 B2 | 5/2016 | Kotidis et al. | |
| 2003/0063284 A1 | 4/2003 | McAndrew et al. | |
| 2008/0128622 A1* | 6/2008 | Weidmann | G01J 3/02 250/343 |
| 2009/0180122 A1 | 7/2009 | Federici | |
| 2009/0225802 A1 | 9/2009 | Day et al. | |
| 2010/0045977 A1 | 2/2010 | Puzey | |
| 2010/0140476 A1 | 6/2010 | Werner et al. | |
| 2011/0080311 A1 | 4/2011 | Pushkarsley et al. | |
| 2012/0033697 A1* | 2/2012 | Goyal | B82Y 20/00 372/45.01 |
| 2012/0062895 A1 | 3/2012 | Rao | |
| 2012/0162659 A1 | 6/2012 | Goldberg et al. | |

OTHER PUBLICATIONS

"610/620-IR, FT-IR Microscopy and Imaging Solutions," Varian, Inc., 2008-2009, pp. 2, 5 and 7.

Capasso, F., "Quantum cascade lasers penetrate the market," Interview by Marie Freebody, Optics & Laser Europe, Feb. 2009, p. 13.

Hinkov, B. et al., "Broad band tunable quantum cascade lasers for stand-off detection of explosives," Proceedings of the SPIE, vol. 7484, Sep. 1, 2009, pp. 748406. Abstract only.

International Preliminary Report on Patentability dated Dec. 27, 2012, from counterpart International Application No. PCT/US2011/040217, filed on Jun. 13, 2011.

International Search Report dated Feb. 7, 2012, from counterpart International Application No. PCT/US2011/040217, filed on Jun. 13, 2011.

Lambrecht, A., et al., "Continuous glucose monitoring by means of fiber-based, mid-infrared laser spectroscopy," Applied Spectroscopy, vol. 60, No. 7, 2006, pp. 729-736. Abstract only.

Mehta, N.K. et al., "Development of an In Situ Spectroscopic Method for Cleaning Validation Using Mid-IR Fiber Optics," BioPharm, May 2002, pp. 36-42 and 71, six pages.

Nicholson, S. "MIR Spectroscopic Sensing: Identify, Measure, Protect," International Quantum Cascade Lasers School & Workshop, Sep. 19, 2008, Cascade Technologies, 26 pages.

So, S.G. et al., "Development of Digital Signal Processor Controlled Quantum Cascade Laser Based Trace Gas Sensor Technology," IEEE Sensors Journal, vol. 6, No. 5, Oct. 2006, pp. 1057-1067.

Wang, P. et al., "Infrared Spectroscopy using Quantum Cascade Lasers," Bruker Optics, School of Engineering and Applied Sciences, Harvard University, Jun. 2009, 19 pages.

Weida, M.J. et al., "Quantum cascade laser based replacement for FTIR microscopy," Daylight Solutions, Proceedings of the SPIE, vol. 7902, 2011, 7 pages.

Wysocki, G. et al., "Widely tunable mode-hop free external cavity quantum cascade laser for high resolution spectroscopic applications," Applied Physics B, Lasers and Optics, Springer-Verlag, vol. 81, 2005, pp. 769-777.

International Preliminary Report on Patentability, dated Aug. 17, 2017, from International Application No. PCT/US2016/016909, filed on Feb. 6, 2016. Eight pages.

* cited by examiner

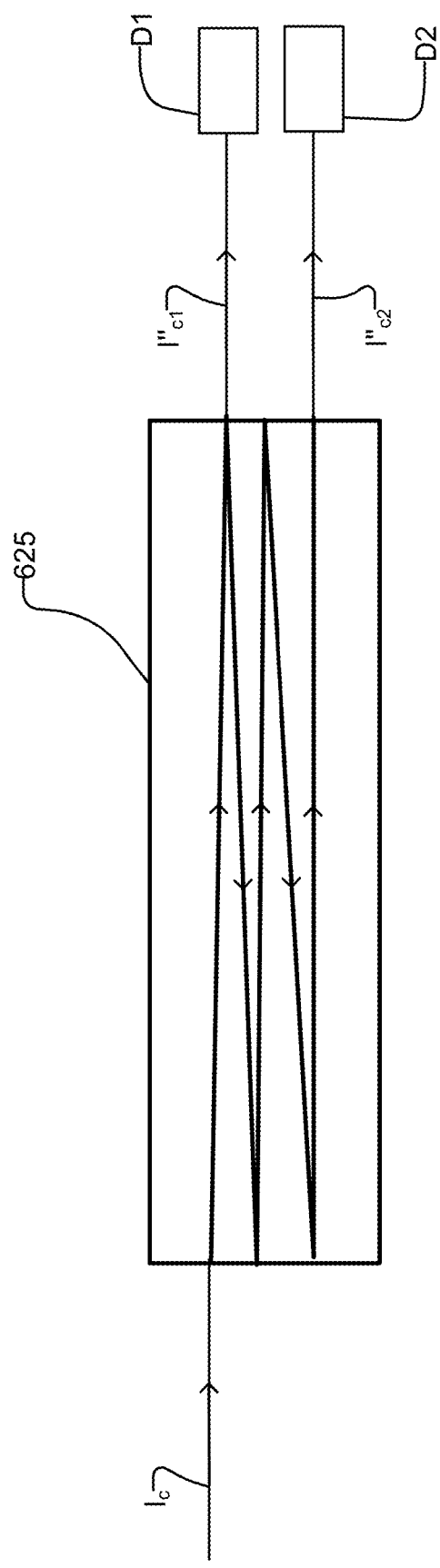

QUANTUM CASCADE LASER (QCL) BASED GAS SENSING SYSTEM AND METHOD

RELATED APPLICATIONS

This application claims priority to U.S. Provisional Application Nos. 62/113,069, filed on Feb. 6, 2015, 62/186,067, filed on Jun. 29, 2015, and 62/262,010, filed on Dec. 2, 2015, all of which are incorporated herein by reference in their entirety.

BACKGROUND OF THE INVENTION

Quantum cascade lasers generate light in the mid- to far infrared (IR) using inter-subband transitions in a repeated stack of semiconductor multiple quantum well heterostructures. A spectroscopy system based on these tunable lasers and various applications for such a system have been discussed by Kotidis et al., in U.S. Pat. No. 8,780,347 B2, entitled "QCL Spectroscopy System and Applications Therefor", which is herein incorporated by reference in its entirety.

SUMMARY OF THE INVENTION

Embodiments of the present principles provide a gas sensing system and method, in which one or more tunable quantum cascade lasers are configured to provide a beam in a wide tunable wavelength range in the infrared region. The laser beam is directed to one or more sample cells with at least two different path lengths for gas detection or sensing by obtaining an absorption spectrum for at least one of the gases or components.

In general, according to one aspect, the invention features a gas sensing system, which includes: at least one quantum cascade laser configured for tuning within a wavelength range and for providing a beam in the wavelength range; at least one cell for containing a sample and for receiving the beam; the at least one cell providing at least two different path lengths for the beam; and a detector system configured for obtaining at least one absorption spectrum for the sample by detecting the beam exiting the at least one cell.

In general, according to another aspect, the invention features a method for gas sensing, which includes: providing at least one quantum cascade laser configured for tuning within a wavelength range and for providing a beam in the wavelength range; directing the beam through at least one cell containing a sample; the at least one cell providing at least two different path lengths for the beam; and obtaining at least one absorption spectrum for the sample by detecting the beam exiting the at least one cell.

The at least one quantum cascade laser can be a plurality of quantum cascade lasers (QCLs) configured for providing a plurality of beams, each of the plurality of beams being in a wavelength range associated with a respective QCL. Optical components are then used to combine the plurality of beams to form a single beam and for directing the single beam through the at least one cell.

In one example, a single cell is used that has the at least two different path lengths for the beam.

In other case, a first cell and a second cell are provided, the first cell having a first path length, and the second cell having a second path length that is different from the first path length.

Multi-pass arrangements can be further be used. Pressure control can also helpful.

In general, according to another aspect, the invention features a gas sensing system. This system comprises at least one quantum cascade laser configured for tuning within a wavelength range and for providing a beam in the wavelength range, at least one cell for containing a gas sample, from a semiconductor processing operation, and for receiving the beam, and a detector system configured for obtaining at least one absorption spectrum for the sample by detecting the beam exiting the at least one cell.

In general, according to still another aspect, the invention features a method for gas sensing. This method comprises providing at least one quantum cascade laser configured for tuning within a wavelength range and for providing a beam in the wavelength range, directing the beam through at least one cell containing a sample from a semiconductor processing operation, and obtaining at least one absorption spectrum for the sample by detecting the beam exiting the at least one cell.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 6B shows an alternative embodiment of the system;

DETAILED DESCRIPTION OF THE PREFERRED EMBODIMENTS

Figure 1A:
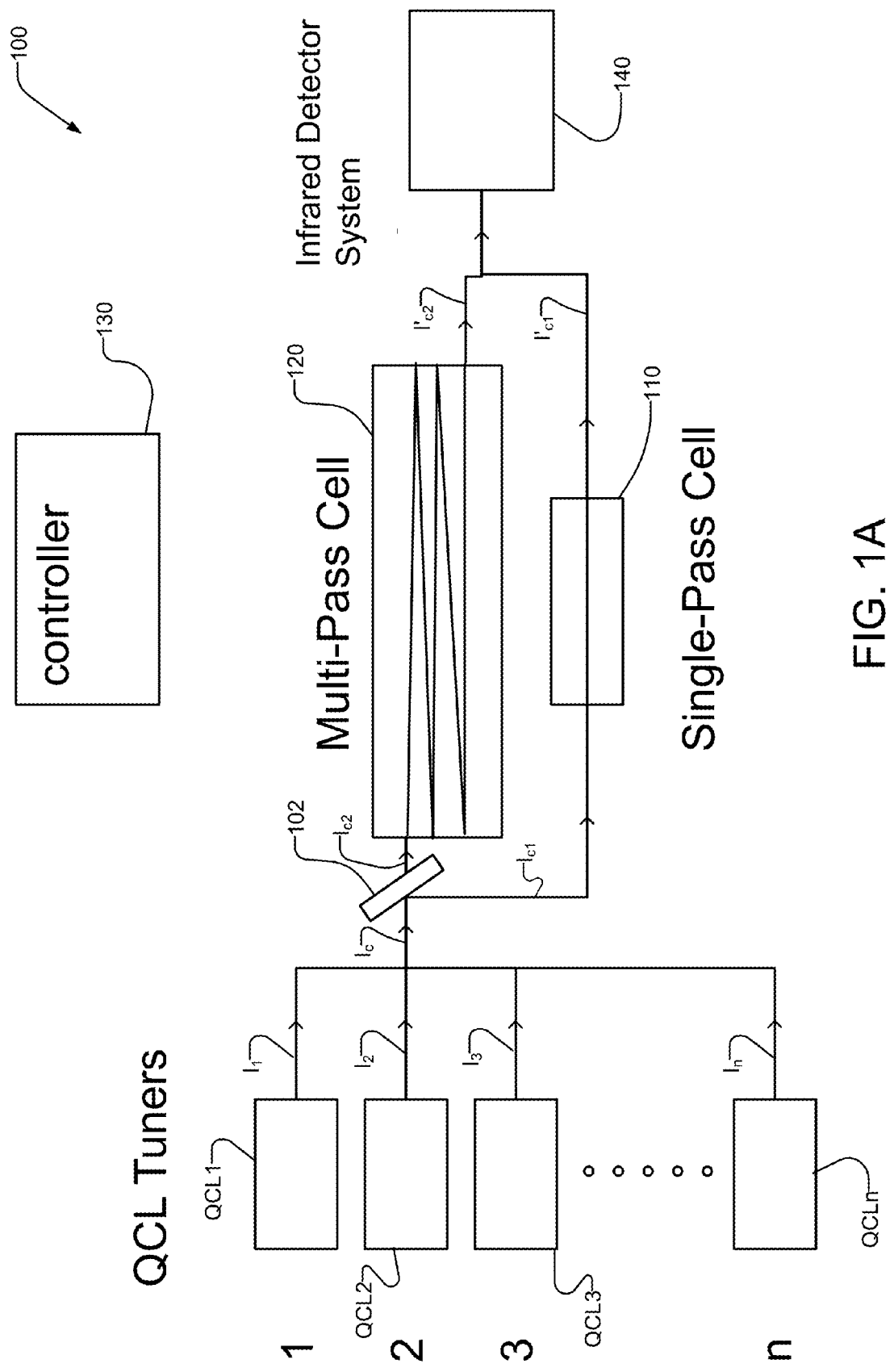
FIG. 1A shows an overview of one embodiment of a QCL gas sensing system of the present invention.
Figure 1B:
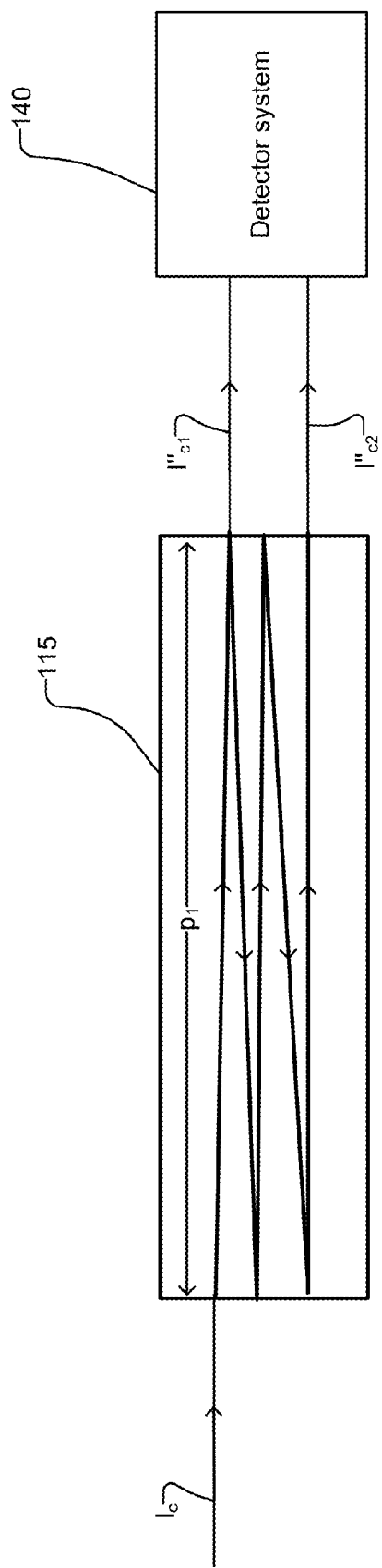
FIG. 1B shows an alternative embodiment of the gas sensing system from FIG. 1A.

FIGS. 1A and 1B show an overview of two embodiments of a gas sensing system 100 of the present invention. By configuring one or more QCLs to provide rapid tuning over a wide wavelength range, the system can be used for rapid gas sensing applications, while providing sufficiently large spectral range to detect multiple gases using their IR absorption characteristics.

Multiple QCL tuner modules QCL1, QCL2, QCLn with different tunable wavelength ranges are used in order to cover the broad spectral range offered by this system in some embodiments. In one embodiment, the gas sensing system can have up to four QCL tuners, but in other embodiments, the number is not limited to four. A single QCL tuner can also be used in still other implementations.

As shown in FIG. 1A, the beams $I_1, I_2, \ldots, I_n$ from the multiple QCL tuner modules are combined into a single beam $I_c$, which is then split by beam splitter 102 into multiple beams $I_{c1}, I_{c2}$ prior to entering two or more gas cells 110, 120, respectively. The gas cells 110 and 120 have different path lengths. For simplicity's sake, the optical components (e.g., folding mirror, dichroic, and partially reflecting mirrors, and so on) used for combining two or more beams $I_1, I_2, \ldots, I_n$ are not shown in FIG. 1A or 1B. Instead, details can be found in various sections of U.S. Pat. No. 8,780,347 B2. It is possible to have any combination of beams going into any combination of gas cells.

FIG. 1B shows another configuration with a single gas cell 115, which has at least two different path lengths for the incoming laser beam $I_c$ (combined beam from one or more QCLs). In this illustration, one path length (p1) corresponds to a single pass through the cell, with beam $I''_{c1}$ exiting the cell and directed to the detector system 140. A second path length (p2) corresponds to a multi-pass through the cell (after 5 passes in this illustration), with beam $I''_{c2}$ exiting the cell and directed to the detector system 140. In one embodiment, the two path lengths are 10 cm and 70 cm, respectively. In general, one path length is less than 40 cm and the other is longer than 50 cm. This embodiment can make the overall system more compact than having separate gas cells. This multi-path length single cell configuration can also have other benefits such as referencing out system level differences with the only difference in optical signal being the difference in path length inside the cell.

The multiple QCL tuner modules (QCL1, QCL2, QCLn) are employed to cover a wider scan band. In one example, each of the modules generates a narrowband, tunable optical signal that scans in wavelength through a different module scanband or wavelength region. The separate modules cover different module scanbands so that the effective scanband of the system covers a wide wavelength band or region such as 5.0 to 13 micrometers in wavelength. In general, the different tunable ranges from the QCL modules do not overlap or have little spectral overlap with each other, although a certain amount of wavelength overlap can be acceptable as long as it does not adversely impact the efficiency or performance of the system.

A controller 130 (e.g., including electronic components such as a processor, memory, and so on) controls the operation of the modules to sweep their tunable optical signals sequentially through their respective module scanbands so that the entire system scanband is covered. The spectral response of the sample (i.e., IR absorption spectrum) is accumulated from the time response of the detector system 140.

In one embodiment, the detector system 140 comprises two photo detector, one photo detector for detecting each incoming beam $I''_{c1} I''_{c2}$.

In another embodiment, beam switches are used so that the beams $I''_{c1} I''_{c2}$ are received at different times at a common photo detector.

In still another embodiment, the single input beam single beam $I_c$ is pulse modulated with pulses of less than a millisecond long with less than a 50% duty cycle. Preferably the pulses are even shorter in duration such as less than a microsecond, or even less than 10 nanoseconds. The beam is then split, the two paths with the different path length provide different delays. As a result, the pulses from the different paths arrive at different times in beams $I''_{c1} I''_{c2}$. Thus, the detector system 140 includes, in one implementation, a single photo detector that detects the pulses in both beams $I''_{c1} I''_{c2}$, albeit separated in time. This is illustrated in more detail below.

One embodiment of the system includes the use of multiple gas or sample cells. The use of multiple gas cells provides the capability to simultaneously measure gases or gas concentrations that might be too absorptive for a long path cell (or long path length), as well as gases that are not very absorptive. The low absorptive gases need a long cell in order to provide enough signal for low limits of detection.

In most cases, long path lengths are provided by using a long cell or multi-pass configuration, in which the combined beam bounces back and forth several times prior to exiting the cell and reaching the detector. Short cells are typically configured for single pass. More than two gas cells can be included in the gas sensing system, depending on the type of gases that need to be monitored. In some cases, it is possible for the long cell to be single pass, for example, as in the case of a duct or pipe.

One application for the gas sensing system is real-time mudlogging analysis (the creation of a detailed record of a borehole in a drilling operation), in which C1, C2, C3, nC4, iC4, nC5 and iC5 compounds and potentially heavier hydrocarbons such as C6, etc., are simultaneously measured by the gas sensing system.

Figure 2A:
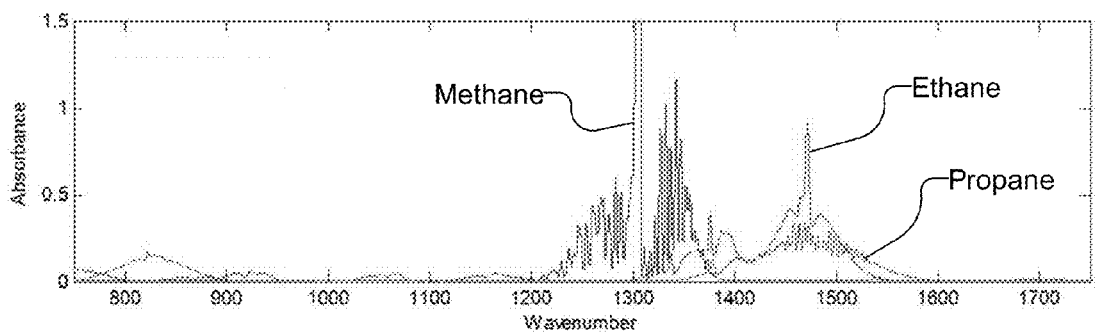
FIG. 2A is a plot of absorbance as a function of wavenumber for methane, ethane, and propane.
Figure 2B:
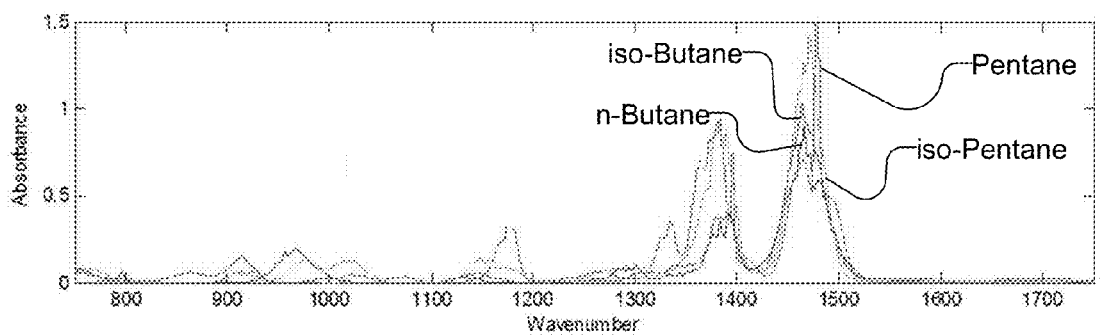
FIG. 2B is a plot of absorbance as a function of wavenumber for n-Butane, iso-Butane, Pentane and iso-Pentane.
Figure 2C:
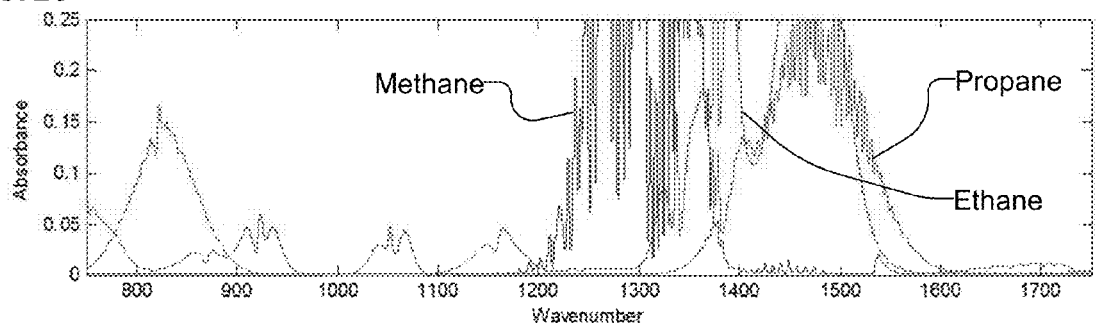
FIG. 2C is a plot of absorbance as a function of wavenumber for methane, ethane, and propane.
Figure 2D:
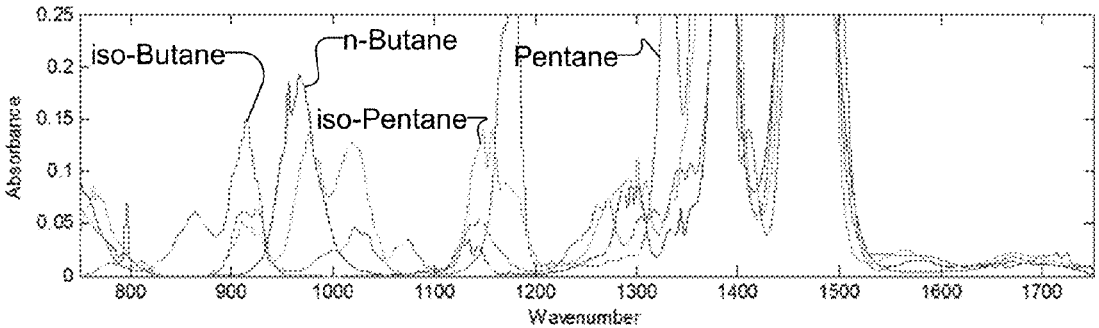
FIG. 2D is a plot of absorbance as a function of wavenumber for n-Butane, iso-Butane, Pentane and iso-Pentane.

FIGS. 2A-2D show the infrared spectra of these hydrocarbons in the range of 5-13 μm or 750 to 1750 in wavenumber ($cm^{-1}$), which is used in one embodiment of the system. As shown, there are regions of strong and weak spectral bands, as well as areas of strong overlap in the IR absorptions of the various compounds. FIGS. 2A and 2B show the large absorption in the 5-8 μm region of the spectrum and FIGS. 2C and 2D provide expanded views to display the lower absorption in the 8-13 μm region of the spectrum. The controller 130 employs algorithms to select the proper combination of QCL ranges that take advantage of the strong absorption bands for the gases being monitored and low overlap with absorption bands from other gases or impurities.

For example, since water absorption occurs in the 5-7.5 µm range, it is desirable to select QCL ranges outside that band and still achieve low limits of detection (i.e., high detection sensitivities) for the sample gases being monitored. Thus, a proper selection of the IR wavelength region can lead to an improved detection sensitivity for a given gas while minimizing spectral interference from other gases. In other words, to enhance the detection sensitivity for a given gas in a sample or mixture, a wavelength range for the QCL laser beam can be selected so that it includes or overlaps with a strong absorption band for the given gas, but has a minimal overlap with absorption bands from another gas or impurity, thus avoiding spectral interference from at least another gas (or impurities) that may be present in the sample.

In the particular case of the C1-C5 Mudlogging monitoring, a long multi-pass cell, e.g., cell 120 or long path in the multi-path cell 150, is primarily used for the detection of the C3-C5 components, because they typically appear in low concentrations during Mudlogging. However, C1 and C2 at low enough concentrations (to avoid signal saturation) can also be measured with this multi-pass cell. The single cell, e.g., cell 110 or short path in the multi-path cell 150, is used primarily for C1 and C2, which typically appear in large concentrations. However, depending on the relative gas concentrations present, the short cell can also be used for the C3-C5 components.

Another embodiment involves the use of pressure control in the gas cells in order to improve the sensitivity of the system. By lowering the pressure in the gas cell, the infrared absorption can be reduced. The system has gas cells with solenoid valves and flow restrictors such as bleed valves and/or pressure regulators that can be used to reduce or increase the pressure of the gas inside the cells. This configuration provides an additional method of controlling the absorption of light by the sample gas or chemical in the cell. Therefore, the optimum absorption of light, i.e. avoiding too much or too low absorption, can be controlled not only by using a combination of short and long path gas cells, but also by controlling the pressure inside the cells, which reduces or increases the-light absorption by the sample gas or chemical. The pressure control is designed in such a way as to minimize the equilibration time when changing configuration.

In one example, the selection of gas cell length and pressure combination is provided in the following ways. In one case, software built-in, user-selectable, look-up tables, prescribe the selection for the desired gas and concentration of interest. For example, methane monitoring at 90% concentration could be accomplished with a short cell (or short path length) and low pressure, while 1% concentration could require the long cell (or longer path length) and higher pressure. In another case, automated software selection senses that the detector gets either saturated or not receiving enough light, in which case the controller applies the appropriate combination of gas cell and pressure automatically, using an intelligent, built-in algorithm. For example, one or more processors in the system can be programmed so that, in response to detected IR signal levels, the controller can take actions to select system parameters and conditions suitable for the specific gas being monitored. The software can also use all the data but the algorithm can weight different sections of data from the cells differently based on saturation levels.

In order to ensure that the measurements are correct, a preconditioning algorithm for the data can be used. The measured spectra are evaluated using preselected criteria, which are built into the system's operational software, and only the spectra that passed the criteria are used as inputs to the prediction model.

In another alternative configuration, the QCL tuners shown in FIG. 1 can include one or more Distributed Feedback (DFB) lasers. Under this "hybrid" configuration, both widely tunable QCL tuners (QCL1, QCL2, e.g.,) are combined with narrow band tuners (QCL3) in a single devices. The narrow band tuner QCL3 includes narrowly tunable (DFB) lasers. The purpose of this alternative configuration is to use the DFB laser tuner(s) (QCL3) to capture the spectral peaks of certain chemicals that are outside the spectral range covered by the widely tunable QCLs. DFB lasers are typically narrowly tunable, so they need to be specifically selected for each targeted gas peak. Multiple DFB lasers can be used to capture multiple gases with typically a one-to-one match, while the widely tunable QCLs can be used to detect multiple gases per laser chip or tuner.

Figure 3:
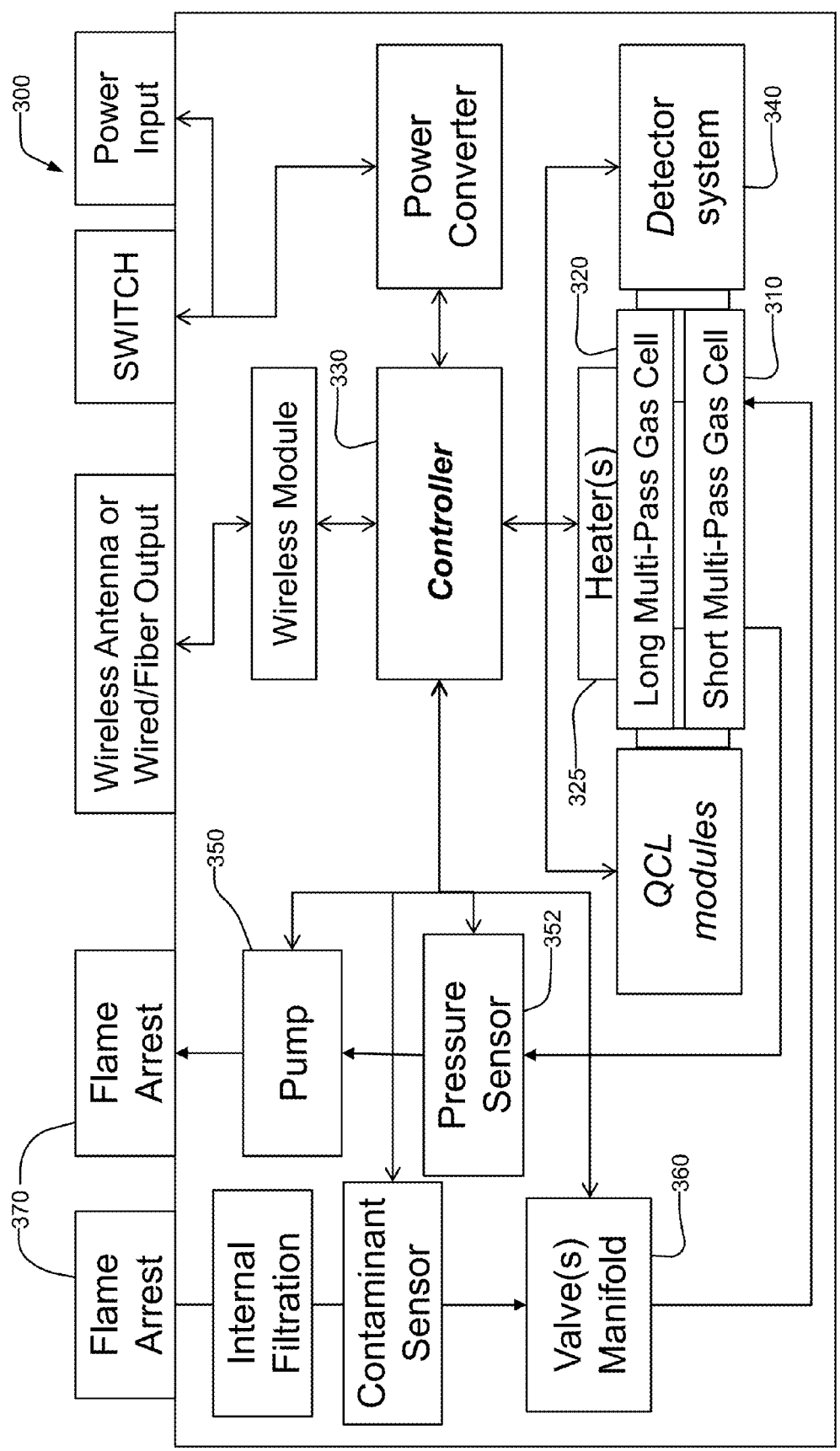
FIG. 3 is a block diagram of some components of a gas sensing system.

FIG. 3 shows a block diagram of an example of a system 300 suitable for use with mud logging application. Details for various components are discussed below.

Gas cells 310, 320: The cell temperature for the one or more cells is designed to be higher than 40° C., around 50° C., which is maintained by using one or more heaters 325. This prevents condensation of hydrocarbon gases in the cell 310 or 320, as the cell body temperature is well above the n-pentane boiling point. Water entering the cell is likely to evaporate, as the water content in the lines will be determined by the equilibrium at the mud surface. Higher temperatures minimize issues with gas chemistry affecting the spectroscopy. However, the elevated temperature cannot prevent heavier hydrocarbons from contaminating cell surfaces. (To avoid contamination by heavier hydrocarbons would require operating the cell at 100-150° C., which is incompatible with operating inside an explosion proof box.) The cell windows (not shown in FIG. 3) are designed to be removable to aid in cleaning, should the cells become contaminated with high-boiling point liquids like ethylene glycol (e.g., used in drying the entering gas) or with heavier hydrocarbons (diesel) that can be present in the drilling environment. Since the operating orientation of the gas sensing instrument or sample cell may not be well-defined, it may not possible to design the gas entrance and exit orifices to be self-draining. Therefore, the orifices are placed so that the entire volume of the cell can be fully swept by the entering gas. The temperature sensor is placed so that the gas temperature can be measured. The measured temperature will be slightly lower than the cell body and will depend on the temperature and flow rate of the incoming gas.

Pump 350: A pump 350 is used for evacuating the gas cells 310 and 320, with pressure being measured by a pressure sensor 352. In one embodiment, the pump is based on the application for C1-C5 measurements, but the general selection criteria would apply to other gases as well. The pump is required to draw about 5 SLPM (standard liter per minute) and provide an ultimate vacuum around 10 mbar or less. The pump is selected to fit in a minimum volume. The flow rate should be sufficiently high to obtain sampling with minimal lag between the sampling point and the gas sensing instrument. The ultimate vacuum is required to empty the cell of as much gas as possible so that an accurate reference can be taken. The ultimate vacuum of 10 mbar means that about 1% of gas remains in the cell. Under most operating conditions, this should be adequate and the prediction module accommodates effects from this that are related to water. Alternately, a pump that operates at ambient conditions can be used in conjunction with "zero" and "span" ports (not shown in FIG. 3) which can route zero air or a calibration standard via an arrangement of valves in order to take a background reference (zero) and also to verify the validity of the reading using a calibration standard (span). The wetted parts of the pump are specified according to the application, for example; a Viton® membrane diaphragm can be employed to obtain a wider operating temperature range and provide some chemical resistance to hydrocarbons. The Viton membrane diaphragm places an operating temperature range of 5-50° C. where the pump meets specifications. Below this range, there is a risk of cracking the diaphragm as it stiffens with the lower temperature.

Valve(s) Manifold 360: The valve selected is designed for natural gas service and small volume. Ideally, the valve provides total shutoff of the gas coming into the cell 310 or 320 and minimal restriction when the valve is open. A normally closed (NC) valve provides some protection to the system when the power is not applied. The interior of the valve and cell is not exposed to ambient gases or migrating particles. The primary purpose of the valve is to provide the ability to pump out the cells 310 and 320, either selectively or simultaneously, to provide a reference measurement. As such, the level of optically absorbing gas in the evacuated cell should be as low as possible. The primary sources of leaks in the system are the gas cell windows, fittings, pump, and the valve. The valve itself is sensitive to particulates, like Teflon shavings. The valve seat is made of soft nitrile. Particulate contaminants cause the valve to seat improperly, creating a leak. Removing the contaminant requires removing the valve and disassembling the valve to access the valve seat. The Teflon flake contamination normally only appears during testing or during reconditioning where pipe threads are connected and disconnected. In normal operation, particulates that the valve is exposed must pass through the steel frit that is present on the inlet side of the explosion proof case in addition to the submicron particle filter inside the system.

Flame Arresters 370: These are added to the system for additional safety in case of internal fire or explosion.

Figure 4:
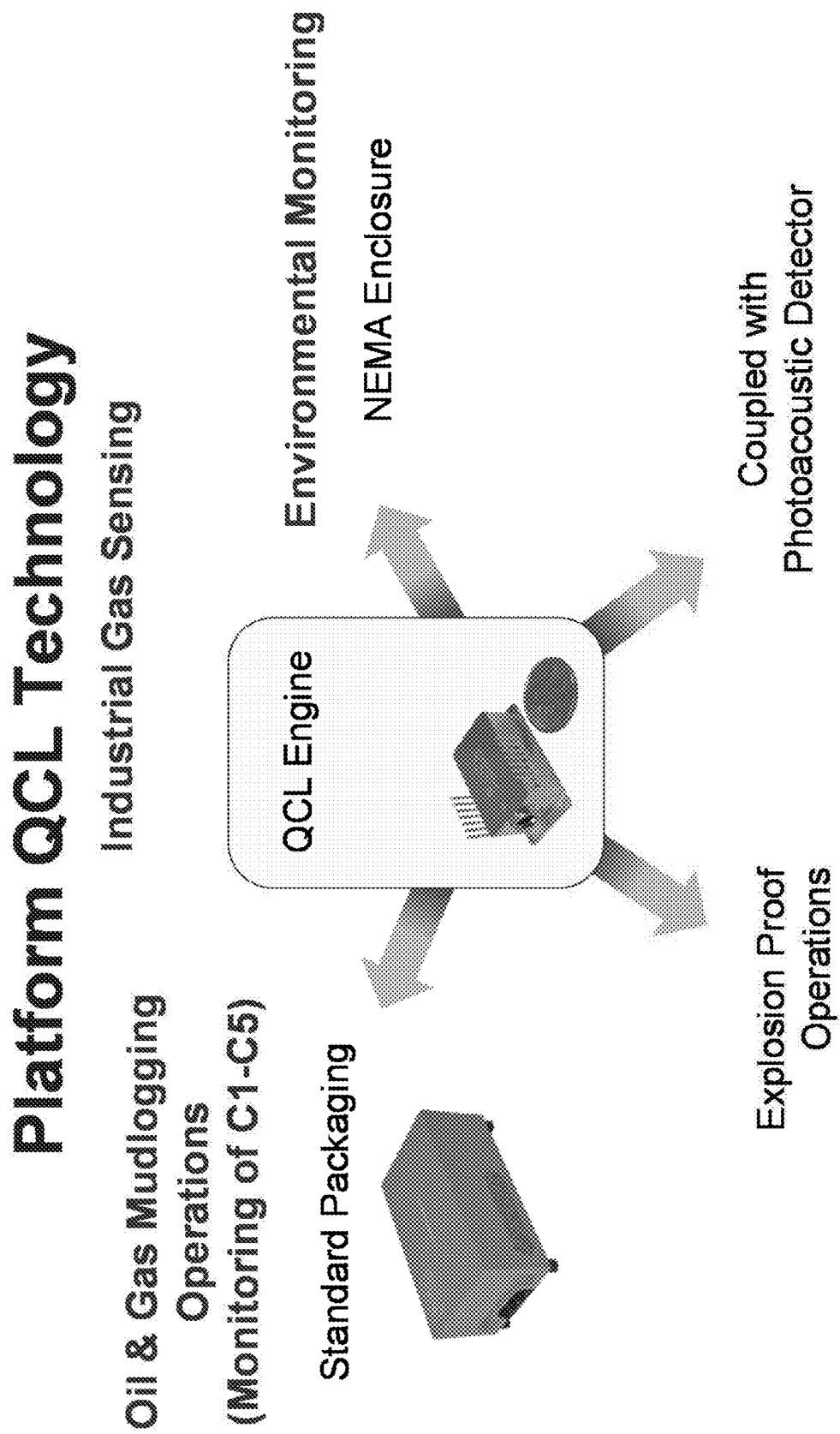
FIG. 4 shows examples of some applications for the QCL system.

FIG. 4 shows additional applications that can be used with the QCL-based gas sensing system. These applications include: monitoring of gases (such as C1-C5) in both oil and gas mudlogging operations; Standard Conditions package (or National Electrical Manufacturers Association, NEMA-type enclosures); applications requiring explosion proof enclosures; photoacoustic sensors for environmental monitoring; handheld devices for lithology and analysis of surface contaminants; and downhole applications, in which high pressure and temperature environments are encountered.

Figure 5:
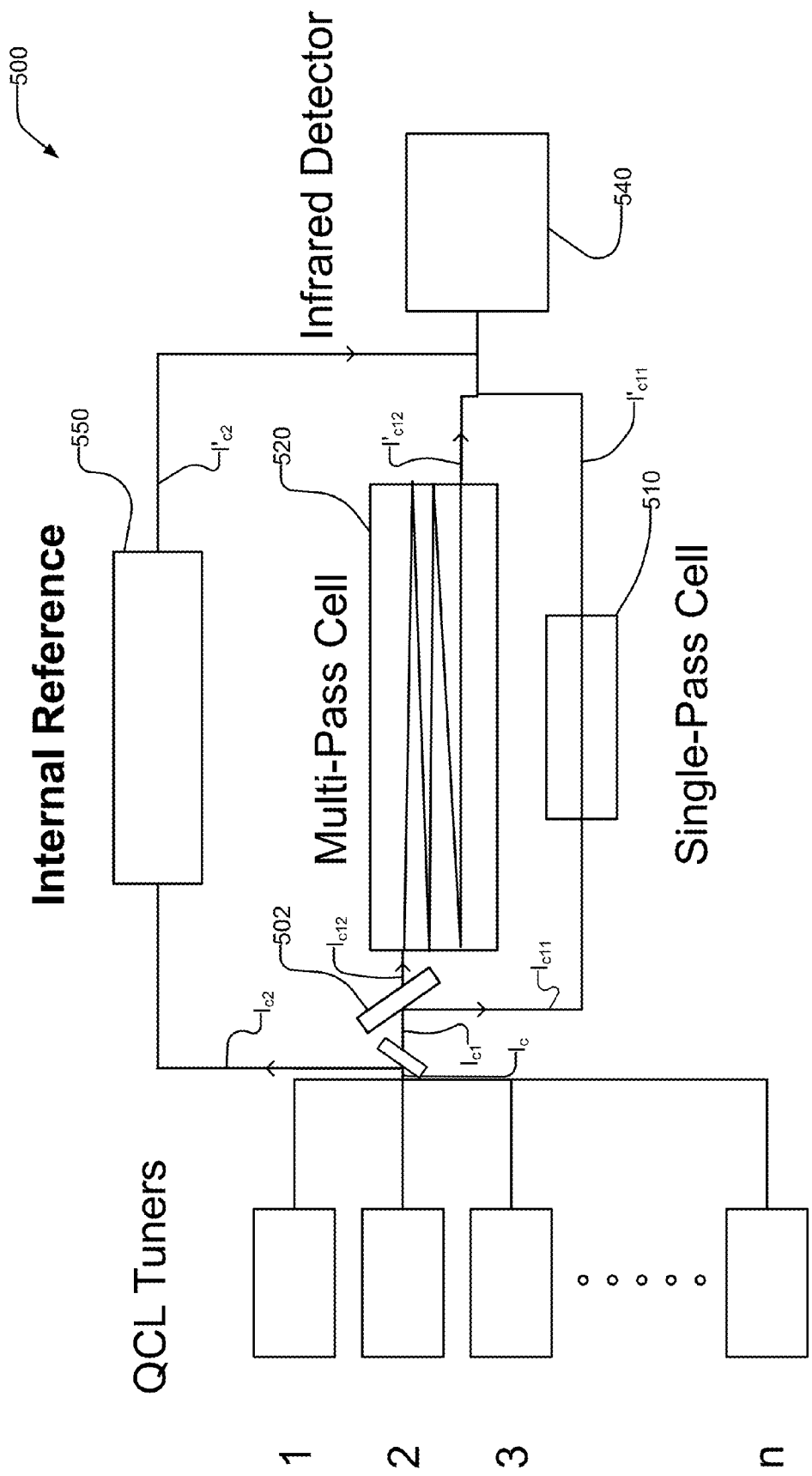
FIG. 5 shows an alternative configuration of the gas sensing system with an internal reference.

FIG. 5 describes an alternative configuration of the system shown in FIG. 1. System 500 includes an additional sample cell 550 used for internal reference purpose. Reference cell 550 contains a known combination of gases, e.g., hydrocarbons, which the system is configured to measure. By providing an internal reference to a gas-standard, variations in system wavelength, power, and/or cavity mode can be corrected on the fly, i.e., in real-time.

As shown, a portion $I_{c2}$ of the light (combined beam $I_c$) from the QCL modules is split and directed through a gas cell 550 containing a sample at a known concentrations ("Internal Reference"), while another portion Iii is further split by beam splitter 502 into two beams $I_{c11}$ and $I_{c12}$, which are directed through the sample cells 510 and 520 and detected by detector system 540.

The reference sample in cell 550 can include one or more gases, and the IR spectrum obtained by detecting beam $I'_{c2}$ at the detector 540 will be compared to a standard or known spectrum of that gas or mixture of gases, which can be retrieved, for example, from a library containing known spectra of various gases for calibration purposes. Any changes in the measured spectrum from the reference cell 550, such as wavelength drift or amplitude calibration, will be corrected by adjusting the factory calibration to match the standard spectrum. This correction can be performed either by a user or automatically at preselected times, or when certain malfunction of the system is observed by an intelligent algorithm, which is populated with a collection of troubleshooting failure modes and their characteristic manifestation on the measured spectra.

Figure 6A:
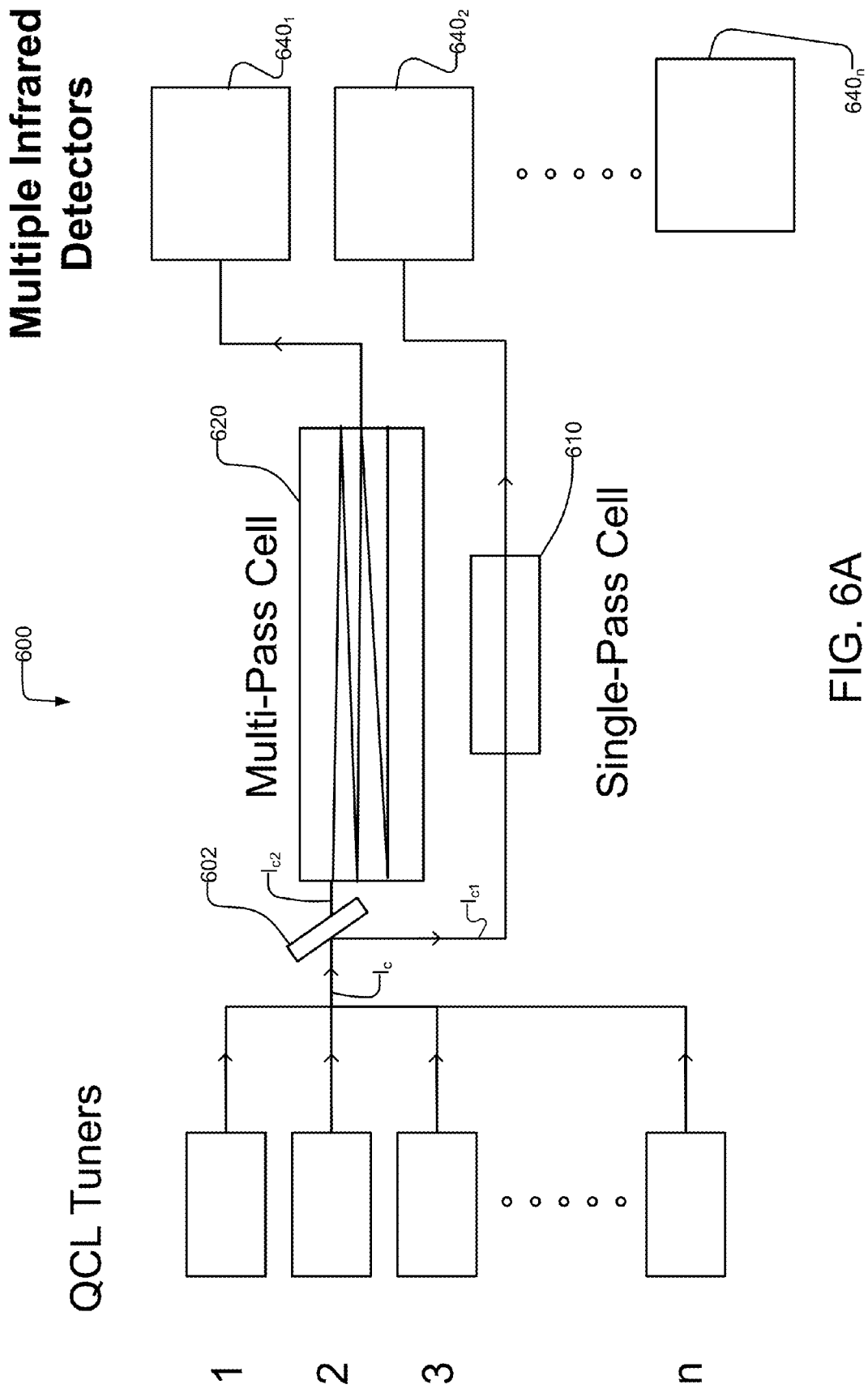
FIG. 6A shows an alternative configuration of the gas sensing system with multiple detectors.

FIG. 6A shows another configuration of a system 600 in which multiple detectors 6401, 6402, . . . , and $640_n$, are used. In this example, the combined beam $I_c$ is split by beam splitter 602 into two portions, $I_{c1}$ and $I_{c2}$, which enter the cells 610 and 620, respectively. As shown in FIG. 6A, detectors $640_1$ and $640_2$ are used for detecting IR beams exiting cells 610 and 620 in order to obtain IR absorption spectra for the respective samples. Typically two detectors are used in order to simplify the system, but more than two could be used, if needed. If more than two sample cells are used, the multiple detectors could be used to separately monitor each cell in order to further optimize the system 600. The schemes shown in other alternative configurations can also be modified for use with multiple detectors. FIG. 6B shows yet another configuration with a single gas cell 625, which has at least two different path lengths for the incoming laser beam $I_c$. In one embodiment, the path lengths are 10 cm and 70 cm, respectively. This dual-path single cell is similar to that shown in FIG. 1B. The two beams $I'_{c1}$ and $I''_{c2}$ exiting cell 625 can be detected by detectors D1 and D2, respectively.

Figure 7:
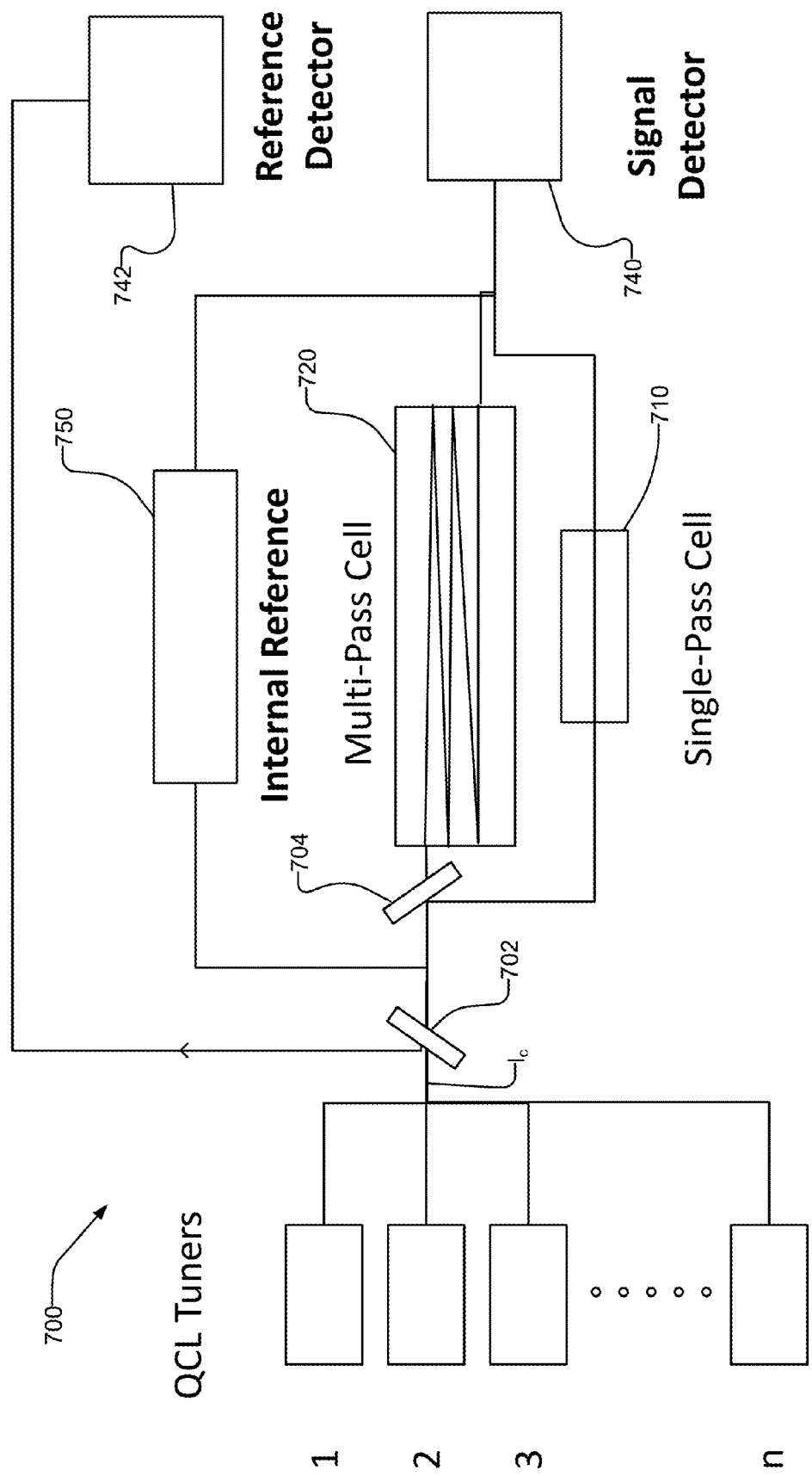
FIG. 7 shows an alternative configuration of the gas sensing system, in which a detector is used for real-time referencing.

FIG. 7 shows another configuration of a system 700 in which a second detector can be used in a real-time referencing scheme. A portion of the combined beam $I_c$ from the QCL modules is split off by beam splitter 702 (prior to entering the cells 710 and 720) and directed to a reference detector 742. This signal is used in real-time to compare with the one measured by a signal detector 740. The other portion of the combined beam $I_c$ that passes through beam splitter 720 is further split into different portions, which are directed to the cells 710, 720 and internal reference cell 750, respectively. The configuration of cells 710, 720 and reference cell 750 is similar to that shown in FIG. 5. As an example, if a pulsed QCL is used as a source, then each pulse can be ratioed to (divided by or normalized to) its original shape, amplitude and wavelength, as recorded by the reference detector 742, which eliminates pulse-to-pulse amplitude and power fluctuations from the laser source. Moreover, the proposed reference detector 742 can be used with all the other alternative configurations listed herein.

Figure 8:
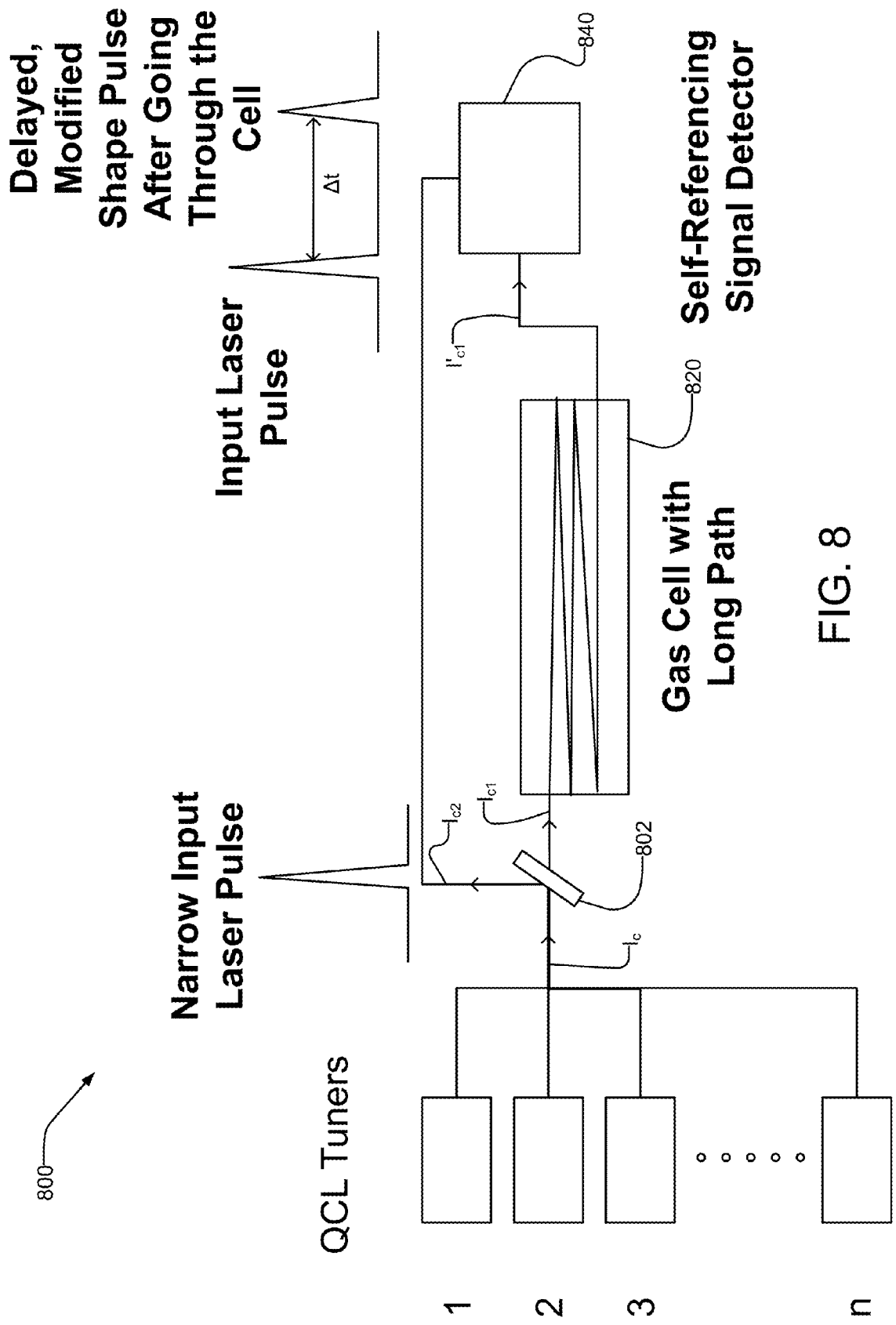
FIG. 8 shows an alternative configuration of the gas sensing system, in which a single detector is used in a self-referencing scheme.

FIG. 8 illustrate the operation in which the input beam is pulse modulated. Specifically it shows a self-referencing scheme using a single detector 840. In this example, a narrow pulse from the QCL combined beam $I_c$ is split by beam splitter 802 into two portions, $I_{c1}$ and $I_{c2}$, which are directed into a long path gas cell 820 and the detector 840, respectively. The beam exiting the cell 820 is a pulse $I'_{c1}$ with a modified shape (compared to $I_{c1}$), which is also directed to the detector 840. The path length of the cell 820 is selected so that the modified pulse $I'_{c1}$ has a sufficiently long time delay ($\Delta t$) with respect to pulse $I_{c2}$ that it is detected as a second pulse by the detector 840, as shown in FIG. 8.

For example, using a 10-30 nanoseconds-wide pulse (feasible with current QCL modules) and a 20 m long gas cell, the delay is about 60 nanoseconds, which is sufficient for separation in time on the detector. Taking ratios of the two pulses, or carrying out other intelligent comparisons between them, such as area, match-filters, spectral composition, etc., the proposed system can provide self-referencing capability in real time.

Figure 9:
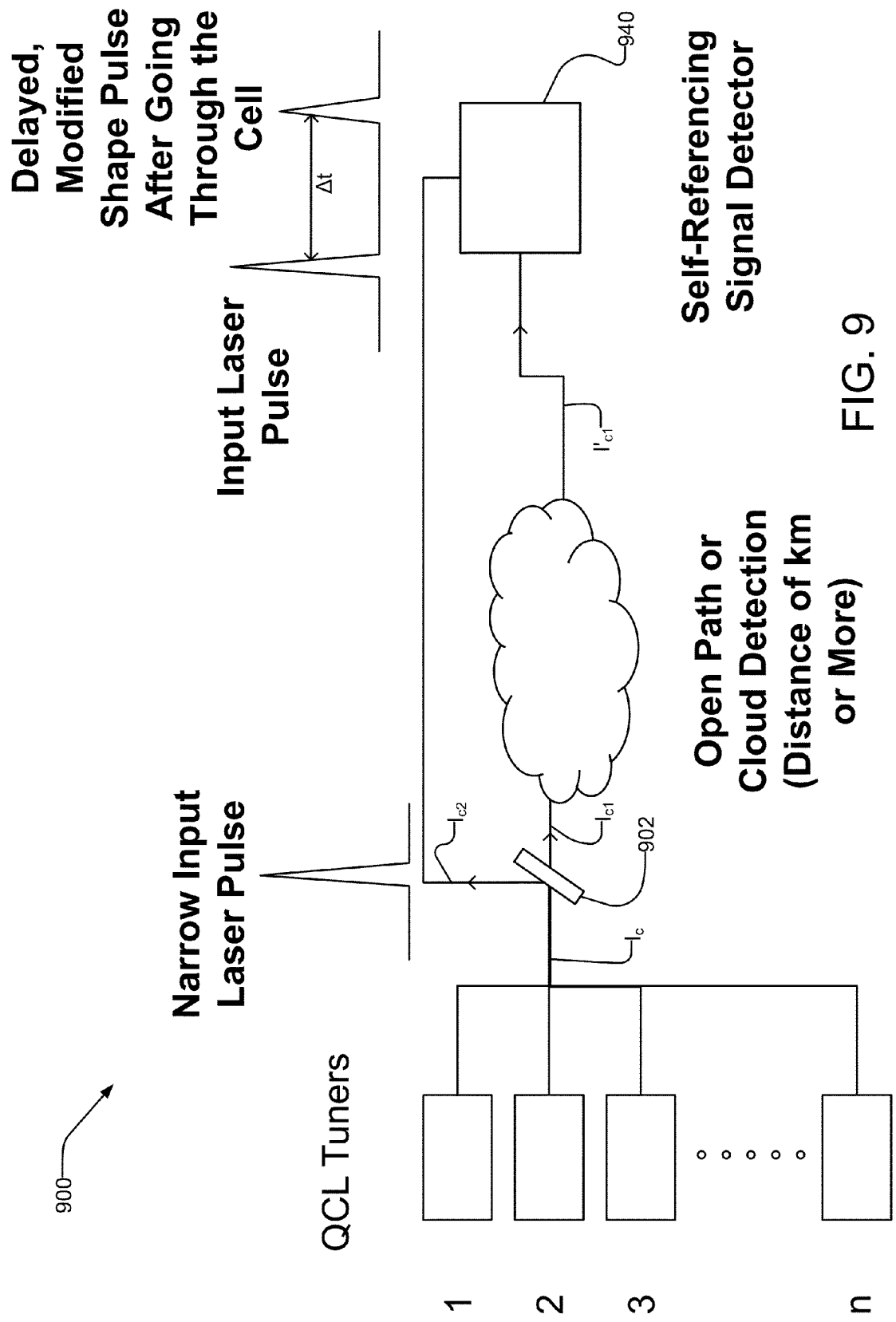
FIG. 9 shows an alternative configuration of the gas sensing system, with an open path providing a long sample length.

FIG. 9 shows an alternative configuration of a system 900 (similar to system 800), except that a long open, free space path (not enclosed or confined) of many kilometers through a region can be used as the "gas cell". In this case, the detector 904 should be configured for detection of both pulses $I_{c2}$ (split off by beam splitter 902) and $I'_{c1}$ after the open path, with the modified pulse $I'_{c1}$ appearing at a much longer time delay ($\Delta t$) compared to pulse $I_{c2}$. Such an open path through a region configuration can be used for different applications in various environmental conditions, e.g., for monitoring samples in the atmosphere, effluent gases around industrial plants, among others.

Figure 10:
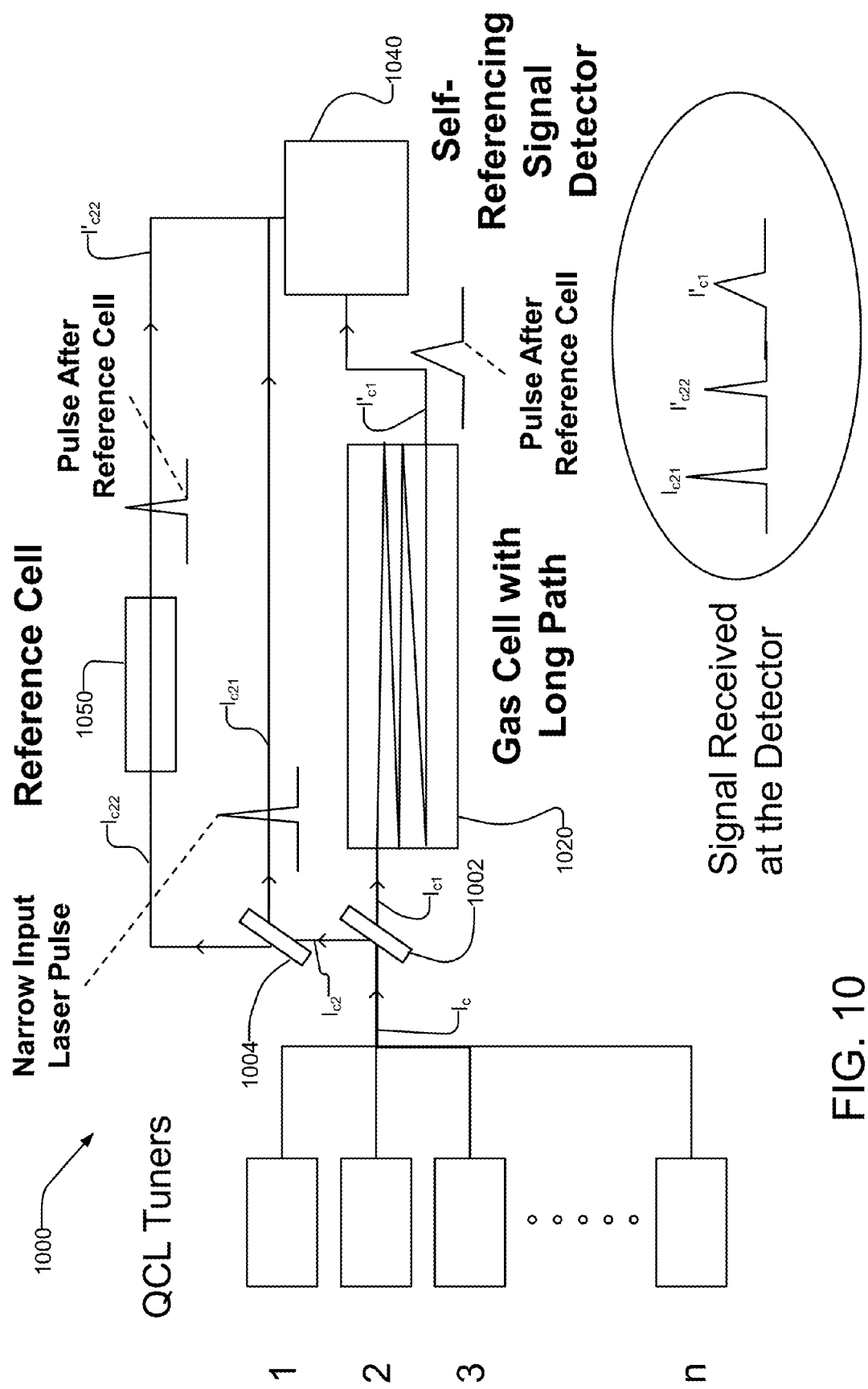
FIG. 10 shows an alternative configuration of the gas sensing system, in which multiple laser pulses are used for self-referencing purpose.

FIG. 10 shows an alternative system 1000, in which the initial laser pulse $I_c$, is split into two portions: $I_{c1}$ and $I_{c2}$, by beam splitter 1002. Pulse $I_{c1}$ enters a long path sample cell 1120, and exits as a modified pulse $I'_{c1}$ that is detected by signal detector 1140. Pulse $I_{c2}$ is further split by splitter 1004 into two portions: $I_{c21}$ and $I_{c22}$. Pulse $I_{c21}$ is directed into detector 1140, while pulse $I_{c22}$ is directed into a reference cell 1050, which has been filled with a standard or reference gas (e.g., at a known concentration). The pulse exiting reference cell 1050 (designated as pulse $I'_{c22}$) is also detected by detector 1140.

Comparisons can be made using the multiple pulses at the detector 1040, with one or more pulses delayed appropriately for even further refinement of the measurements. In that case, a train of several pulses, e.g., two or three, can be detected by the signal detector 1040. In this example, pulse $I_{c21}$ (a portion of the original pulse $I_c$, which has not passed through any sample cell) is first detected, followed by pulse $I'_{c22}$ from the reference cell 1050 (e.g., modified by the absorption of the reference gas, with time delay), and then modified pulse $I'_{c1}$ from the long path cell 1020. Comparisons of these IR signal pulses can be made in real-time to provide information for self-referencing purpose or to correct for variations in one or more system parameters.

Figure 11:
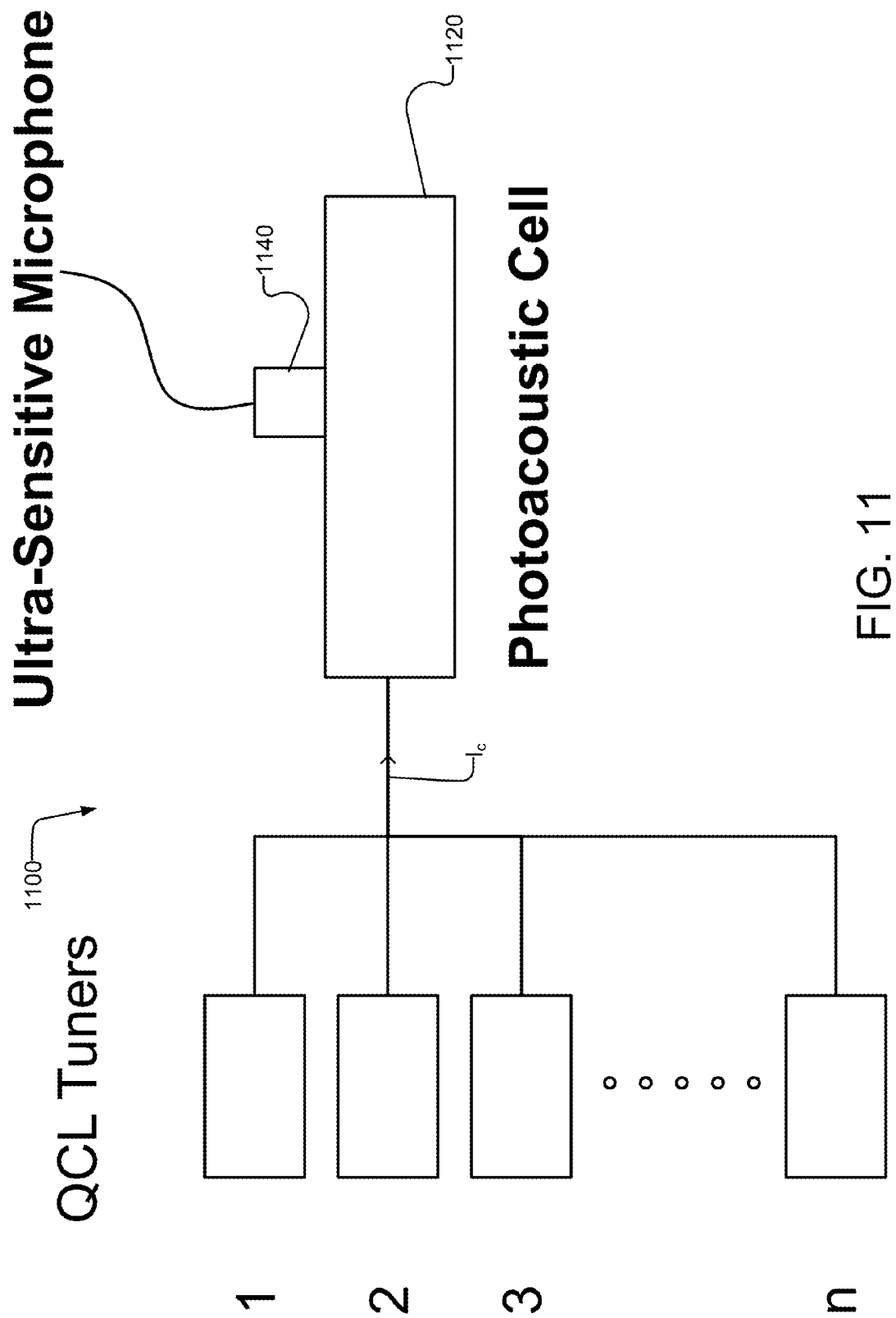
FIG. 11 shows an alternative configuration of the gas sensing system used for photoacoustic gas sensing.

FIG. 11 shows another possible configuration of a system 1100, in which the QCLs can be used as a source for photoacoustic gas sensing. The light or beam $I_c$ from the QCL is used to heat the gas sample in the cell 1120 and the acoustic waves that are generated due to the heating of the gas are detected by a sensitive microphone 1140. Special algorithms can be used to analyze the received signals and gas detection is accomplished, due to the fact that absorption of the light and acoustic propagation are characteristic to each gas.

Figure 12:
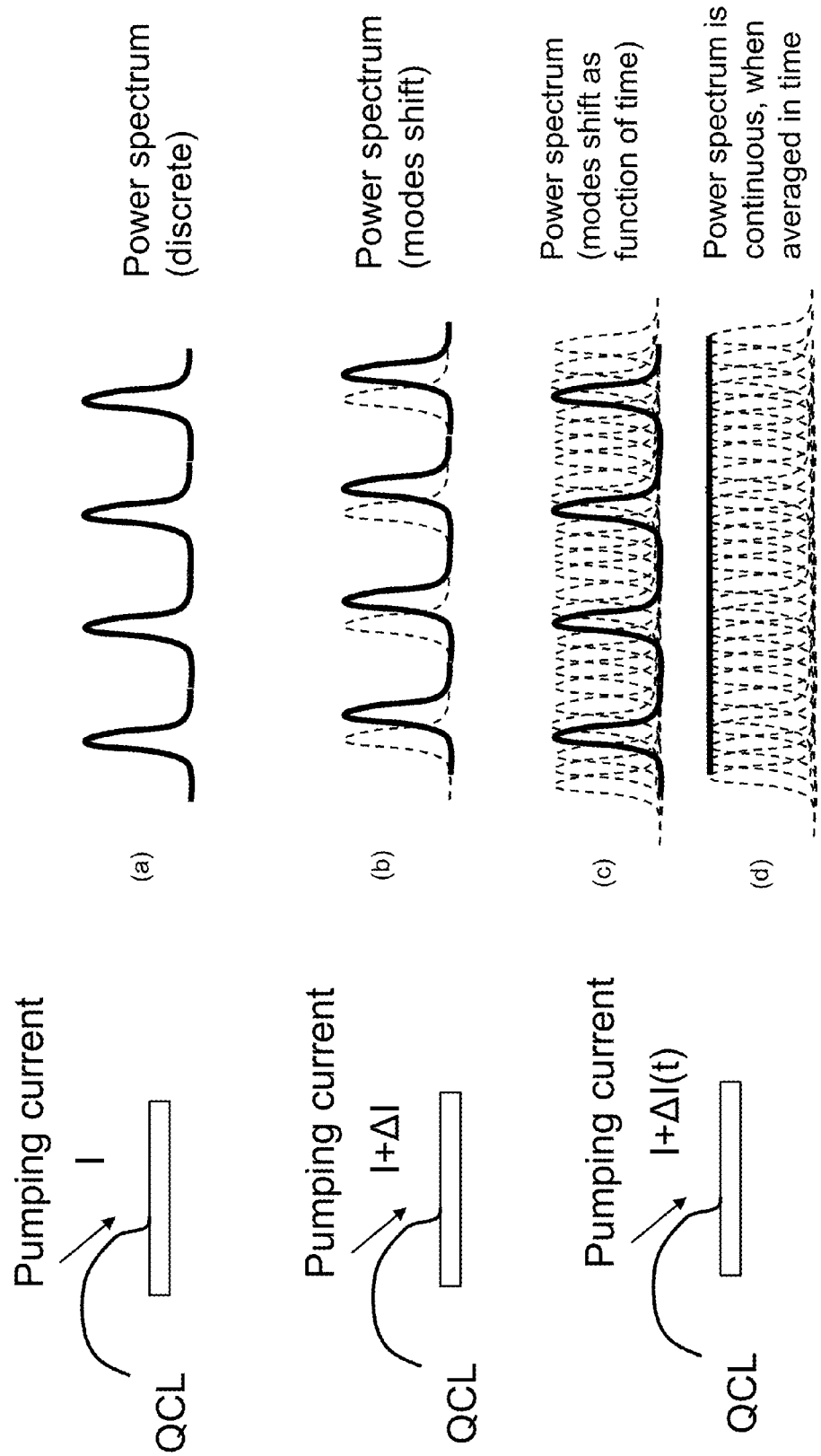
FIG. 12 shows an alternative configuration of the gas sensing system, which has a continuous laser output spectrum.

FIG. 12 shows a configuration in which fast pulsing, slow modulation of the baseline DC current and fast cavity sweep of a QCL are used to provide an output spectrum that is continuous in wavelength. As shown in plot (a) of FIG. 12, the power spectrum of the QCL in the external cavity configuration is not continuous because the laser cavity modes are discrete. The cavity modes are generated by both the laser chip itself (internal cavity) and the external cavity. The internal cavity mode's center wavelength and the mode spacing are determined by the waveguide's refractive index and length. By applying a bias DC current, the local temperature of the waveguide can be modulated, which changes the center wavelength and mode spacing. This is illustrated in plot (b) of FIG. 12, where $\Delta I$ represents a change in the DC current (i.e., bias), and the dashed line represents the resulting mode shifting. By varying the DC bias, the internal modes can be moved back and forth in wavelength (spectrally). Plot (c) of FIG. 12 shows the mode shifting as a function of time when the bias current is varied with time (t) ($I+\Delta I(t)$). Plot (d) of FIG. 12 shows that, by averaging in time, the output power spectrum becomes continuous. If the bias DC current is lower than the threshold, it will not change the laser pulse's characteristics.

Figure 13:
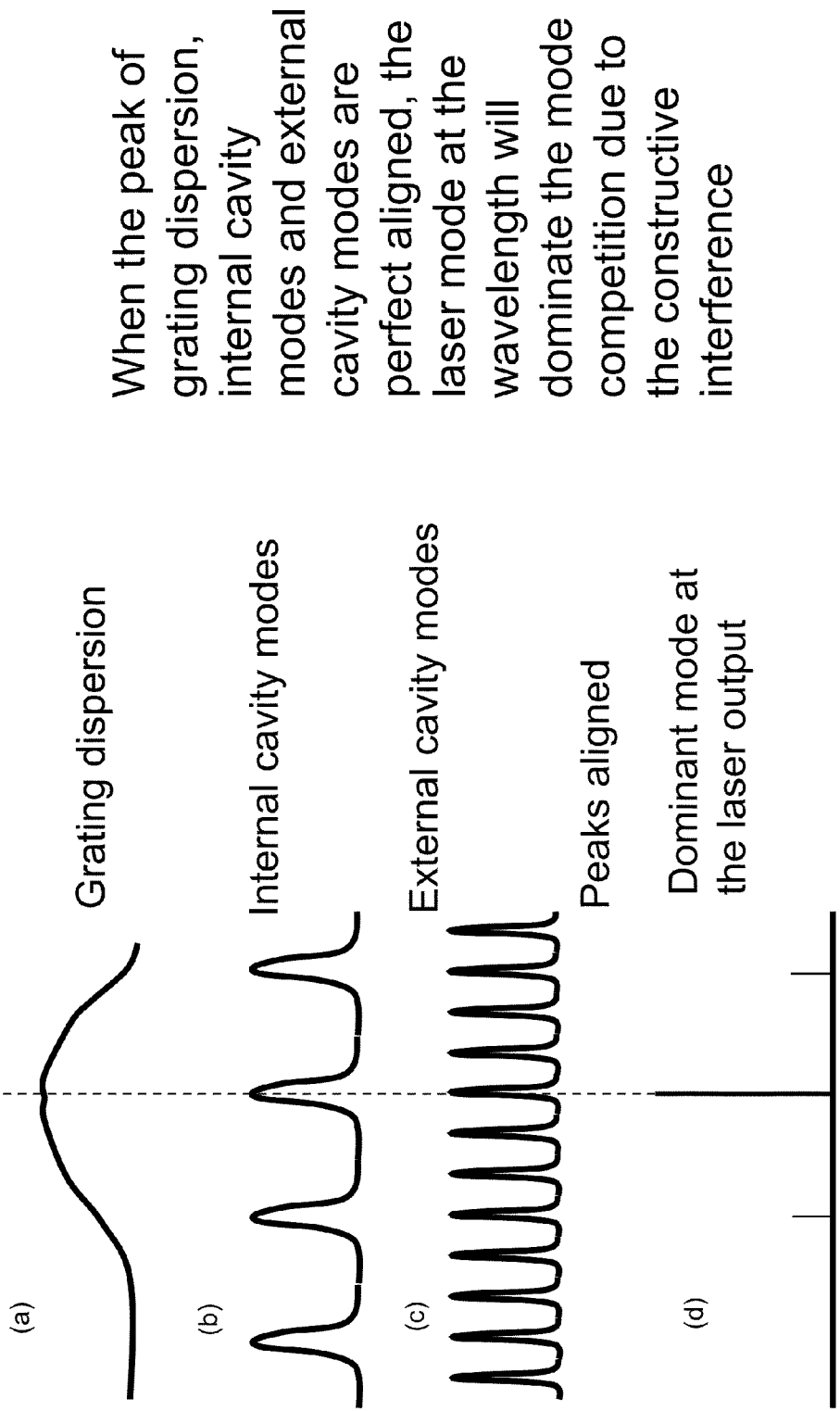
FIG. 13 shows an alternative configuration of the gas sensing system, in which a QCL module is configured for quasi-single mode lasing.

FIG. 13 shows another alternative configuration, in which quasi-single mode lasing for each laser pulse can be achieved by modulating the pumping, baseline DC current. In normal operation, the pulse width of the QCL is very wide, the line width is not transform limited, and there is still mode competition during each pulse. In the QCL in the external cavity configuration, each laser mode is an interference result from the grating dispersion (plot (a)), the external cavity modes (plot (c)), and the internal cavity modes (plot (b)). If at the peak of the grating dispersion, the external cavity mode and the internal cavity mode are perfectly overlapped at a single wavelength, the mode at that wavelength will win the mode competition and be dominant due to constructive interference, as shown in plot (d) of FIG. 13. By adjusting pulse parameters, pumping level, and temperature set point, the internal cavity mode and external cavity mode can be adjusted to align them to the peak of the grating dispersion to generate a quasi-single mode lasing for each pulse. In this operation mode, although there are still some side modes, the majority of the pulse power is concentrated in the main laser mode.

Gas Detection for the Semiconductor Industry Using Mid-Infrared Lasers

Embodiments of the gas sensing system can also be used as a gas analyzer for demanding applications in the semiconductor industry that require both high-speed and high-sensitivity analysis. The gas sensing systems are unique in that they use mid-infrared (MIR) laser technology. This enables multi-gas analysis with sensitivities at the parts-per-billion level (depending on the gas) and with measurement times of less than 1 second. The standard configuration is as an in-line process monitoring and control. The system can be customized based on user requirements.

Mid infrared spectroscopy is a well-developed and proven method for the quantification of gas concentrations. Historically, MIR spectroscopy has required Fourier-Transform Infrared (FTIR) spectrometers which use heated filaments as the source of light. To enable dramatically enhanced performance, widely tunable MIR lasers based on quantum cascade laser (QCL) technology are utilized. QCLs are highly reliable semiconductor lasers that operate over the so-called "molecular fingerprint region" from 5 to 13 microns. The gas sensing system is integrated into a miniature package that is capable very fast wavelength tuning to allow high-speed spectroscopy. The system is capable of making measurements in <0.1 s. However, measurements are typically averaged over >0.5 s to achieve high sensitivity.

The system operates by measuring the transmission spectrum through a gas cell with a heated volume (area) such as an oven. Laser-based gas analyzers have many advantages over FTIR-based systems. For example, since laser beams from the laser tuner remain collimated over long distances, very long-path gas cells can be used. Since the lower detection limit (LDL) improves with increasing length of the gas cell, laser-based systems can achieve LDLs that are more than 10-times better than with an FTIR. Furthermore, as compared to gas cells designed for use with FTIRs, those designed for use with lasers can be made to have much smaller volume. This is important in some applications, e.g., monitoring of semiconductor processing, where fast measurements are required and where the refresh-rate of the gas cell can be a limiting factor.

Table 1 gives examples of several gases along with their LDL when using the standard gas cell having a path length of 6 meters. Since gas cells with path lengths of >100 meters are available, the LDL can be further reduced by a factor of 10 below the values given in Table 1 if required.

TABLE 1

| Gas | Lower Detection Limit (measurement time = 0.5 sec) |
|---|---|
| Silicon tetrafluoride ($SiF_4$) | 0.04 ppm |
| Carbon tetrafluoride ($CF_4$) | 0.02 ppm |
| Nitrogen trifluoride ($NF_3$) | 0.2 ppm |
| Methane ($CH_4$) | 0.5 ppm |
| Xylene ($C_8H_{10}$) | 2.8 ppm |
| Formaldehyde ($CH_2O$) | 2.1 ppm |
| Ammonia ($NH_3$) | 0.9 ppm |

Lower Detection Limit (LDL) for a several process gases using a gas cell. The detection limit can be reduced up to 10× using a longer gas cell.

A more expansive list of semiconductor process gases that can be detected with the present system is as follows: $H_2O$, CO, $CO_2$, $CH_4$, $NH_3$, plus other hydrocarbons; fluorocarbons: $CF_4$, $C_2F_4$, $C_2F_6$, $C_3F_6$, $C_3F_8$, $C_4F_6$, $C_4F_8$, $C_5F_8$; hydro-fluoro-carbons: $CH_2F_2$, $CH_3F$, $CHF_3$, $C_2H_3F$, $C_2HF_3$; silicon-containing: $SiF_4$, $SiH_4$, $SiCl_2H_2$; other fluorine-containing: HF, $SF_6$, $NF_3$, $ClF_3$, $OF_2$, $SOF_2$, $SO_2F_2$; other chlorine-containing: $CCl_4$, $BCl_3$; nitrogen oxides: NO, $N_2O$, $NO_2$; and sulfur oxides: $SO_2$.

Another related application is gas purity characterization. A list of gases that can be detected for purity by the present system includes: impurities in bulk gases such as He, $H_2$, Ar, $O_2$, $N_2$, $H_2O$, $CH_4$, $C_2H_6$, $NH_3$, $CO_2$, CO; impurities in rare gases such as He, Ne, Kr, Xe, Rn; impurities in semiconductor gases such as $H_2$, $SiH_4$, $SiF_4$, HBr, $CF_4$, $CCl_4$, $NF_3$, $C_2F_6$, $C_3F_8$, $N_2O$, $C_2H_2$, $C_2H_6$, $C_3H_4$, $PH_3$, $AsH_3$, $SF_6$, $NH_3$; trace impurities in gases such as $H_2$, Ne, Ar, $N_2$, Kr, CO, $CO_2$, $CH_4$; and sulfur, sulfur compounds, $H_2S$.

Figure 14:
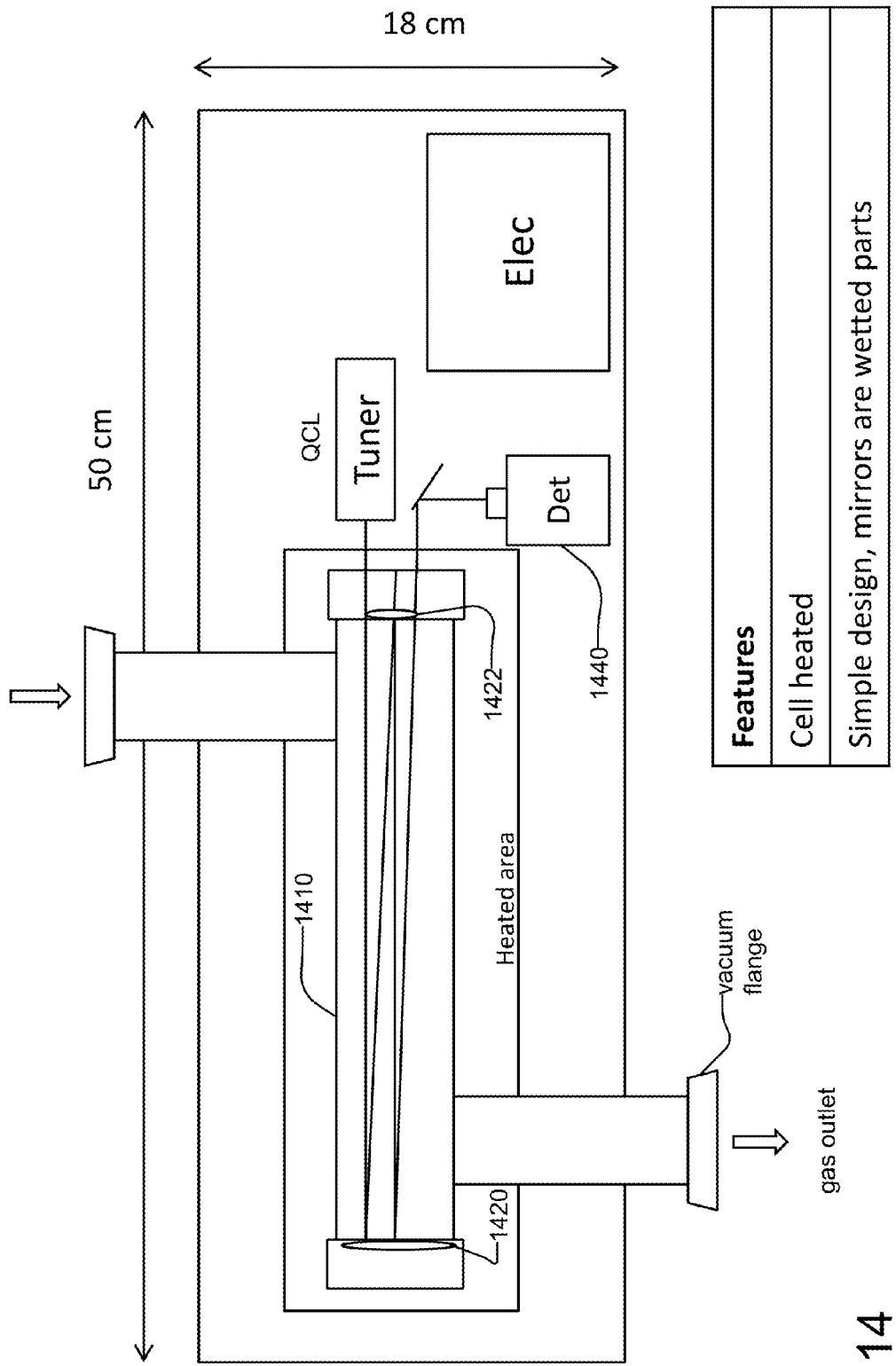
FIG. 14 shows an alternative configuration of the gas sensing system, in which the sample cell mirrors are provided inside a sample cell.
Figure 15:
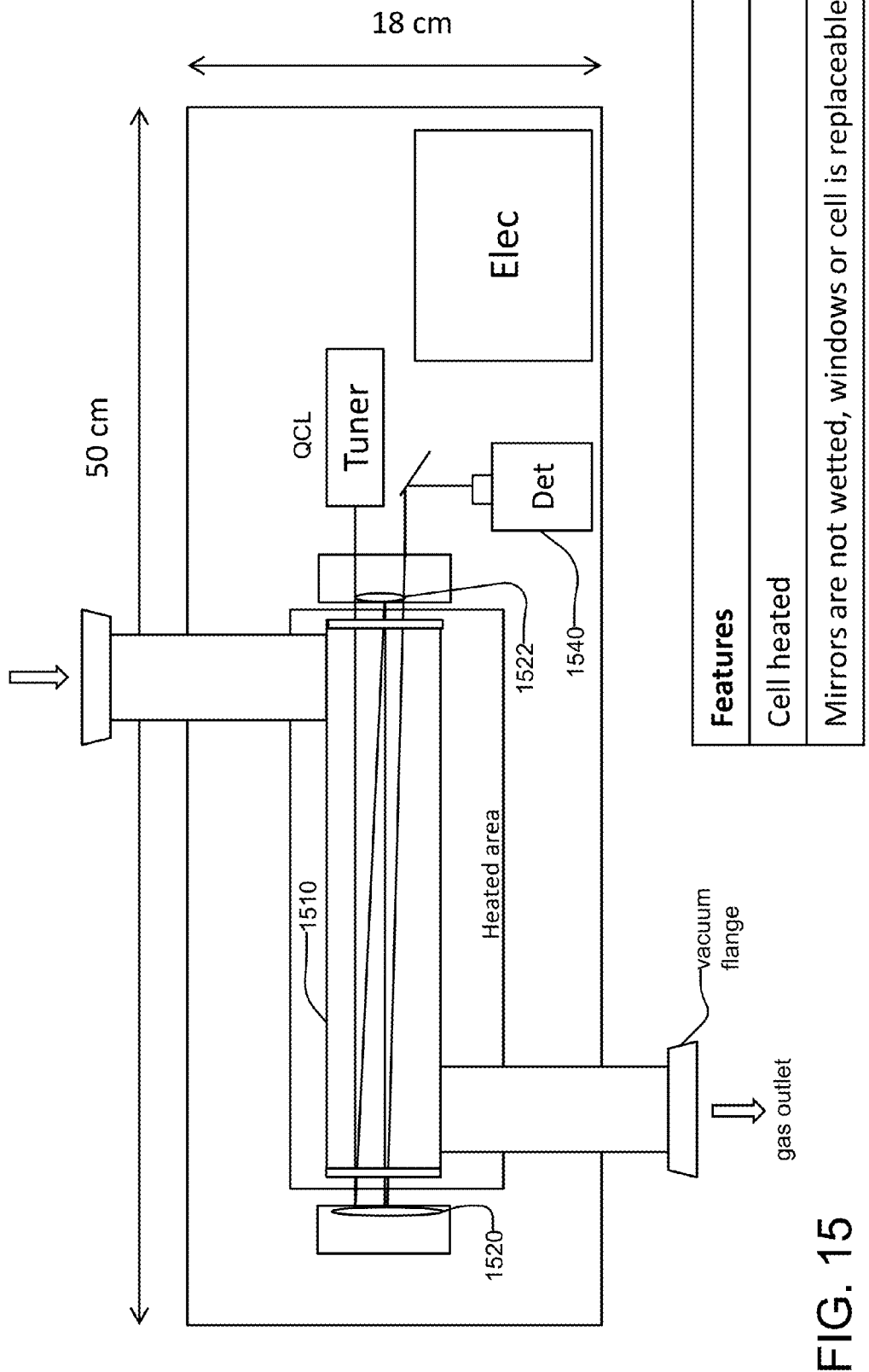
FIG. 15 shows an alternative configuration of the gas sensing system, in which the sample cell mirrors are provided outside a sample cell.

There are two variants to the multi-pass gas cell configuration that can be used to detect the above identified gases. FIG. 14 shows a configuration that has mirrors 1420 and 1422 inside the gas cell 1410, with the IR beam exiting the gas cell being detected by detector 1440. FIG. 15 shows the other configuration with mirrors 1520 and 1522 outside the gas cell 1510, and the IR beam exiting the gas cell being detected by detector 1540.

One advantage of the QCL-based gas sensing system is its fast sample rate, with a laser source that covers the spectral range of interest, coupled to an optical cell that is in-line with the process such that there is no need to transport the sample to the monitoring instrument (thus, avoiding any loss of time).

An important feature of the in-line cell confirmation is a negligible pressure drop across the process.

One application for this technology is in the semiconductor fabrication process. Specifically, this QCL-based system can be used for detecting the endpoint of the semiconductor process, i.e., providing real-time information as quickly as possible that the "process is complete". In one example, $SiF_4$ is produced as a byproduct of an etching process, and once the etching is complete, the $SiF_4$ concentration makes a small step change down (a sudden drop in concentration), which signals the process is complete. It is critical to stop the process as quickly as possible upon the drop in the $SiF_4$ concentration. In this application, the QCL-based gas sensing system monitors the progress of the etch process and then generates a shut-off signal when this $SiF_4$ drop is detected. Another example is chamber cleaning, in which the same byproduct ($SiF_4$) is produced when fluorine-containing compounds ($CF_4$, $C_2F_6$, $NF_3$) are injected to clean or react with silicon residues on the chamber surfaces. The chamber is "clean" when the $SiF_4$ concentration drops off (indicating the Si is fully consumed). Here, when the QCL-based gas sensing system detects the drop in $SiF_4$ concentration, it stops the injection of these fluorine-containing compounds as quickly as possible.

While this invention has been particularly shown and described with references to preferred embodiments thereof, it will be understood by those skilled in the art that various changes in form and details may be made therein without departing from the scope of the invention.

What is claimed is:

1. A gas sensing system, comprising:
    at least one quantum cascade laser configured for tuning within a wavelength range and for providing a beam in the wavelength range;
    at least one cell for containing a sample, the at least one cell receiving the beam, the at least one cell providing at least two different path lengths for the beam through the same sample; and
    a detector system configured for obtaining at least one absorption spectrum for the sample by detecting the beam exiting the at least one cell;
    wherein a second of the two path lengths is several times longer than a first of the two path lengths through the same sample; and the second path length is provided by a multi-pass through the at least one cell.

2. The system of claim 1, wherein the at least one quantum cascade laser is a plurality of quantum cascade lasers (QCLs) configured for providing a plurality of beams, each of the plurality of beams being in a wavelength range associated with a respective QCL;
    the system further comprises optical components for combining the plurality of beams to form a single beam and for directing the single beam through the at least one cell.

3. The system of claim 2, wherein the single beam directed through the at least one cell has a wavelength range equal to a sum of the tunable wavelength ranges associated with the plurality of QCLs.

4. The system of claim 1, comprising a single cell having the at least two different path lengths for the beam.

5. The system of claim 1, wherein the at least one cell comprises a first cell and a second cell both containing the sample, the first cell having a first path length, and the second cell having a second path length that is different from the first path length.

6. The system of claim 1, wherein a first path length is provided by a single pass.

7. The system of claim 1, wherein the at least two different path lengths are 10 cm and 70 cm, respectively.

8. The system of claim 1, wherein the sample comprises a mixture of gases.

9. The system of claim 8, wherein the beam is provided in a wavelength range selected to provide high detection sensitivity for at least one of the gases in the sample, while avoiding spectral interference from at least another of the gases in the sample.

10. The system of claim 1, wherein the at least one cell is configured for pressure control.

11. The system of claim 1, wherein the system is configured for analyzing the sample associated with one of: mud logging and semiconductor processing operations.

12. A method for gas sensing, comprising:
providing at least one quantum cascade laser configured for tuning within a wavelength range and for providing a beam in the wavelength range;
directing the beam through at least one cell containing a sample; the at least one cell providing at least two different path lengths for the beam through the same sample, wherein a second of the two path lengths is several times longer than a first of the two path lengths through the same sample; and
the second path length is provided by a multi-pass through the at least one cell; and
obtaining at least one absorption spectrum for the sample by detecting the beam exiting the at least one cell.

13. The method of claim 12, wherein the at least one quantum cascade laser is a plurality of quantum cascade lasers (QCLs) configured for providing a plurality of beams, each of the plurality of beams being in a wavelength range associated with a respective QCL; the method further comprises:
combining the plurality of beams to form a single beam and directing then single beam through the at least one cell.

14. The method of claim 13, further comprising providing the single beam in a wavelength range equal to a sum of the tunable wavelength ranges associated with the plurality of QCLs.

15. The method of claim 12, further comprising providing a single cell having the at least two different path lengths for the beam.

16. The method of claim 12, wherein the at least one cell comprises a first cell and a second cell, the first cell having a first path length, and the second cell having a second path length that is different from the first path length.

17. The method of claim 12, wherein the first path length is provided by a single pass through the cell.

18. The method of claim 12, wherein the at least two different path lengths are 10 cm and 70 cm, respectively.

19. The method of claim 12, further comprising providing pressure control for the at least one cell.

* * * * *